(12) United States Patent
Goldin

(10) Patent No.: US 6,663,573 B2
(45) Date of Patent: Dec. 16, 2003

(54) BIPOLAR MAPPING OF INTRACARDIAC POTENTIALS USING RECESSED ELECTRODES

(75) Inventor: Alexander Goldin, Haifa (IL)

(73) Assignee: Biosense, Inc., New Brunswick ( * ) Notice: Subject to any disclaimer, the term of this patent is extended or adjusted under 35 U.S.C. 154(b) by 0 days.

(21) Appl. No.: 10/160,417

(22) Filed: May 31, 2002

(65) Prior Publication Data
US 2002/0151807 A1 Oct. 17, 2002

Related U.S. Application Data

(62) Division of application No. 09/612,490, filed on Jul. 7, 2000, now Pat. No. 6,408,199.

(51) Int. Cl.[7] ............................................. A61B 5/04
(52) U.S. Cl. ...................................................... 600/508
(58) Field of Search ............................... 600/508–509, 600/515, 518, 547, 372–374, 381; 607/115, 116, 119, 121–123

(56) References Cited

U.S. PATENT DOCUMENTS

| | | | |
|---|---|---|---|
| 4,532,924 A | 8/1985 | Auth et al. | 128/303.17 |
| 4,682,596 A | 7/1987 | Bales et al. | 128/303.14 |
| 4,852,580 A | 8/1989 | Wood | 128/693 |
| 4,892,102 A | 1/1990 | Astrinsky | |
| 4,945,912 A | 8/1990 | Langberg | 128/642 |
| 4,966,597 A | 10/1990 | Cosman | 606/50 |
| 5,078,714 A | 1/1992 | Katims | 606/38 |

(List continued on next page.)

FOREIGN PATENT DOCUMENTS

| | | |
|---|---|---|
| EP | 0 950 421 A1 | of 0000 |
| EP | 158298 | 10/1985 |
| EP | 0 965 302 A2 | 12/1999 |
| EP | 1 005 838 A1 | 6/2000 |
| WO | WO 90/07303 | 7/1990 |
| WO | WO 94/00050 | 1/1994 |
| WO | WO 96/05768 | 2/1996 |
| WO | WO 97/12548 | 4/1997 |
| WO | WO 97/24981 A3 | 7/1997 |
| WO | WO 97/24981 A2 | 7/1997 |
| WO | WO 97/29701 | 8/1997 |
| WO | WO 98/43547 | 10/1998 |
| WO | WO 99/05971 | 2/1999 |
| WO | WO 99/39650 | 8/1999 |
| WO | WO 00/15130 A3 | 3/2000 |
| WO | WO 00/15130 A2 | 3/2000 |

OTHER PUBLICATIONS

European Search Report dated Sep. 21, 2001 application No. EP 01 30 5855.

Pallas–Areny, Ramon; Webster, John G.; Bioelectric Impedance Measurements Using Synchronous Sampling; IEEE Transactions on Biomedical Engineering, vol. 40, No. 8 Aug. 1993; pp. 824–829.

(List continued on next page.)

Primary Examiner—Kennedy Schaetzle
Assistant Examiner—Kristen Droesch
(74) Attorney, Agent, or Firm—Louis J. Capezzuto

(57) ABSTRACT

A method for measuring near-field electrical activity at a location in a heart comprising introducing into the heart a catheter. The catheter comprises an elongated tubular body having a distal region and a circumferential recess along the length of the distal region, a first electrode mounted on the distal region in close proximity to the circumferential recess, and a second electrode mounted within the circumferential recess. The distal region is positioned at the location in the heart so that the first electrode is in direct contact with heart tissue and the second electrode is not in direct contact with heart tissue but is in contact with blood. A first signal is obtained with the first electrode, and a second signal is obtained with the second electrode. The first signal and the second signal are compared to obtain the near-field electrical activity at the location in the heart.

20 Claims, 7 Drawing Sheets

U.S. PATENT DOCUMENTS

| | | | |
|---|---|---|---|
| 5,282,840 A | 2/1994 | Hudrlik | 607/28 |
| 5,341,807 A * | 8/1994 | Nardella | 600/381 |
| 5,398,683 A * | 3/1995 | Edwards et al. | 600/374 |
| 5,409,000 A | 4/1995 | Imran | 128/642 |
| 5,419,767 A | 5/1995 | Eggers et al. | 604/114 |
| 5,447,519 A | 9/1995 | Peterson | |
| 5,447,529 A | 9/1995 | Marchlinski et al. | 607/99 |
| 5,454,809 A | 10/1995 | Janssen | 606/41 |
| 5,469,857 A | 11/1995 | Laurent et al. | 128/710 |
| 5,494,042 A | 2/1996 | Panescu et al. | 128/695 R |
| 5,546,951 A | 8/1996 | Ben-Haim | 128/710 |
| 5,562,721 A | 10/1996 | Marchlinski et al. | 607/99 |
| 5,577,509 A | 11/1996 | Panescu et al. | 128/696 |
| 5,598,848 A | 2/1997 | Swanson et al. | 128/696 |
| 5,609,622 A | 3/1997 | Soukup et al. | |
| 5,626,576 A | 5/1997 | Janssen | 606/41 |
| 5,662,108 A | 9/1997 | Budd et al. | 128/642 |
| 5,673,704 A | 10/1997 | Marchlinski et al. | 128/739 |
| 5,718,241 A | 2/1998 | Ben-Haim et al. | 128/702 |
| 5,738,096 A | 4/1998 | Ben-Haim | 128/653.1 |
| 5,749,914 A * | 5/1998 | Janssen | 607/2 |
| 5,792,185 A | 8/1998 | Burton et al. | 607/116 |
| 5,833,621 A | 11/1998 | Panescu et al. | 600/509 |
| 5,836,874 A | 11/1998 | Swanson et al. | 600/374 |
| 5,836,875 A | 11/1998 | Webster, Jr. | 600/374 |
| 5,836,990 A | 11/1998 | Li | 607/28 |
| 5,891,095 A | 4/1999 | Eggers et al. | 604/114 |
| 5,935,079 A | 8/1999 | Swanson et al. | 600/509 |
| 5,944,022 A | 8/1999 | Nardella et al. | 128/899 |
| 5,954,719 A | 9/1999 | Chen et al. | |
| 5,991,650 A | 11/1999 | Swanson et al. | |
| 6,064,905 A | 5/2000 | Webster, Jr. et al. | 600/424 |
| 6,075,180 A | 6/2000 | Sharber et al. | |
| 6,201,387 B1 * | 3/2001 | Govari | 128/899 |

OTHER PUBLICATIONS

Promotional Brochure for TaCCor Catheter Ablation System; taCCor, Inc., 1837 Kempton Rd., Charleston, SC; 2 pp.

Plonsey, Robert; Barr, Roger C.; A Critique of Impedence Measurements in Cardiac Tissue; Annals of Biomedical Engineering, vol. 14, 1986; pp. 307–322.

Rush, Stanley, Ph.D.; Abildskov, J.A., M.D.; McFee, Richard, Ph. D.; Resistivity of Body Tissues at Low Frequencies; Circulation Research, vol. XII, Jan. 1963; pp. 40–50.

Panescu, Dorin; Whayne, James G.; Fleischman, Sidney D.; Mirotznik, Mark S.; Swanson, David K.; Webster, John G.; Three–Dimensional Finite Element Analysis of Current Density and Temperature Distributions During Radio–Frequency Ablation; IEEE Transactions on Biomedical Engineering, vol. 42, No. 9, Sep. 1995; pp. 879–890.

* cited by examiner

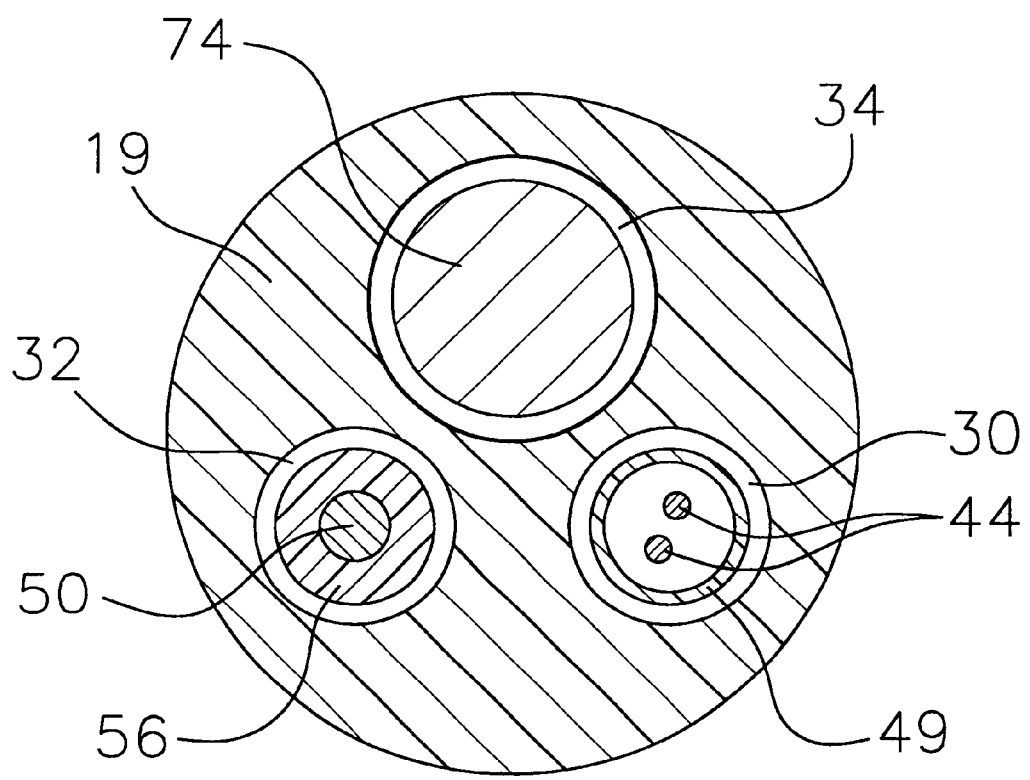

BIPOLAR MAPPING OF INTRACARDIAC POTENTIALS USING RECESSED ELECTRODES

This is a division of application Ser. No. 09/612,490 filed Jul. 7, 2000, now U.S. Pat. No. 6,408,199.

The present invention is related to other commonly owned U.S. patent applications: U.S. Ser. No. 09/611,849, entitled Catheter with Tip Electrode Having a Recessed Ring Electrode Mounted Thereon; U.S. Ser. No. 09/611,617, entitled Mapping and ablation Catheter; U.S. Ser. No. 09/612,487, entitled Multi-Electrode Catheter, System and Method; and U.S. Ser. No. 09/612,606, entitled System and Method for Detecting Electrode-Tissue Contact; all commonly owned by the assignee of the present invention and the disclosures of each are incorporated by reference herein in their entirety.

FIELD OF THE INVENTION

The present invention is directed to a method for measuring electrical activity in the heart and a catheter useful for performing the method.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

In healthy humans the heartbeat is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signal potentials throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation is a procedure often successful in terminating cardiac arrhythmia. This procedure involves applying sufficient energy to the interfering tissue to ablate that tissue thus removing the irregular signal pathway. However, before the ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with or in close proximity to the endocardium. By monitoring the electrical signals at the endocardium, aberrant conductive tissue sites responsible for the arrhythmia can be pinpointed.

Once the origination point for the arrhythmia has been located in the tissue, the physician may use an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

Conventional unipolar electrode catheters utilize a primary tip or ring electrode that cooperates with a reference electrode outside the patient's body. Such catheters are known to map inaccurate electrical readings due to the reference electrode being located outside the patient's body.

Previous attempts have been made to design a bipolar electrode catheter having two electrodes within the patient's body. However, such catheters also have limited accuracy. Specifically, both electrodes pick up near field electrical signals emanating from the conductive endocardial tissues due to their contact with the heart tissue, and far-field electrical signals which propagate from other regions of the heart due to their contact with the blood. The far-field signals interfere with the near-field signals, making accurate measurement of the near-field signals difficult. Accordingly, a need exists for a bipolar electrode catheter that more accurately measures near-field signals.

U.S. Pat. No. 5,749,914 to Janssen discloses a catheter for removing obstructions from a tubular passageway in a patient. In one embodiment, Janssen describes a catheter having a distal end with a recessed annular ridge that defines a groove in which a plurality of electrodes are seated. The electrodes are sized so that they are recessed within the annular ridge. A return electrode is located on the catheter proximal to the recessed electrodes. The electrodes are connected to a radio-frequency energy source that generates and supplies current to the electrodes to ablate constructive material. Janssen nowhere teaches or suggests, however, using this catheter to map electrical activity in the heart.

U.S. Pat. No. 4,966,597 to Cosman discloses a cardiac ablation electrode catheter with a thermosensing detector at a position in the distal end of the catheter. In one embodiment, the ablation electrode has an insulative exterior with openings that provide exposed electrode surfaces. Each of the electrode surfaces can be independently connected to different contacts, which are then connected to a voltage source, or the electrode surfaces can all be connected together. A temperature-measuring conductor is attached to one or more of the electrode surfaces. The object of the invention described in Cosman is to provide a cardiac catheter for tissue ablation with ultra-fast faithful recording of temperature in the affected tissue. Cosman nowhere discloses, however, obtaining electrical signals with different electrodes and comparing the signals to obtain near-field electrical activity information.

SUMMARY OF THE INVENTION

The present invention is directed to a catheter having two electrodes for bipolar mapping and a method for using the catheter. In one embodiment, the invention is directed to a method for measuring near-field electrical activity at a location in a heart. The method comprises introducing into the heart a catheter comprising an elongated tubular body having a distal region and a circumferential recess along the length of the distal region. A first electrode is mounted on the distal region in close proximity to the circumferential recess.

A second electrode is mounted within the circumferential recess. The method further comprises positioning the distal region at the location in the heart so that the first electrode is in direct contact with heart tissue and the second electrode is not in direct contact with heart tissue but is in contact with blood. A first signal is obtained with the first electrode, and a second signal is obtained with the second electrode. The first signal and the second signal are compared to obtain the near-field electrical activity at the location in the heart.

In another embodiment, the invention is directed to a method for measuring near-field electrical activity at a location in a heart comprising introducing into the heart a catheter comprising an elongated body having an outer diameter and a distal region, a first electrode mounted on the distal region, and a second electrode mounted on the distal region in close proximity to and electrically isolated from the first electrode, the second electrode having an outer diameter less than the outer diameter of the portion of the distal region on which it is mounted. The distal region is positioned at the location in the heart so that the first electrode is in direct contact with heart tissue and the second electrode is not in direct contact with heart tissue but is in contact with blood. A first signal is obtained with the first electrode, and a second signal is obtained with the second electrode. The first signal and the second signal are compared to obtain the near-field electrical activity at the location in the heart.

In still another embodiment, the invention is directed to a method for measuring near-field electrical activity at a location in a heart comprising introducing into the heart a catheter comprising an elongated body having a distal region, a first electrode mounted on the distal region, and a second electrode mounted on the distal region in close proximity to and electrically isolated from the first electrode. The second electrode is covered by a blood-permeable membrane that prohibits direct contact between the second electrode and surrounding heart tissue. The distal region is positioned at the location in the heart so that the first electrode is in direct contact with heart tissue and the second electrode is not in direct contact with heart tissue but is in contact with blood. A first signal is obtained with the first electrode, and a second signal is obtained with the second electrode. The first signal and the second signal are compared to obtain the near-field electrical activity at the location in the heart.

In yet another embodiment, the invention is directed to a catheter comprising an elongated body having a distal region. A first electrode is mounted on the distal region. A second electrode is mounted on the distal region in close proximity to and electrically isolated from the first electrode. The second electrode is covered by a blood-permeable membrane that, in use, prohibits direct contact between the second electrode and surrounding heart tissue.

DESCRIPTION OF THE DRAWINGS

These and other features and advantages of the present invention will be better understood by reference to the following detailed description when considered in conjunction with the accompanying drawings wherein:

FIG. 7 is an end cross-sectional view of the tip section depicted in FIG. 6.

DETAILED DESCRIPTION

Figure 1:
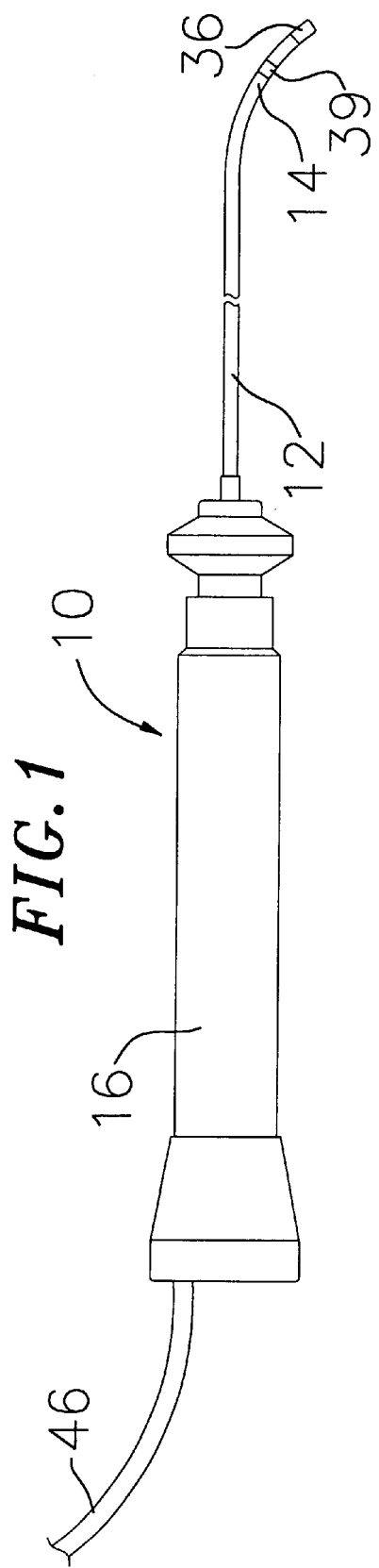
FIG. 1 is a side view of an embodiment of the catheter of the invention.
Figure 2:
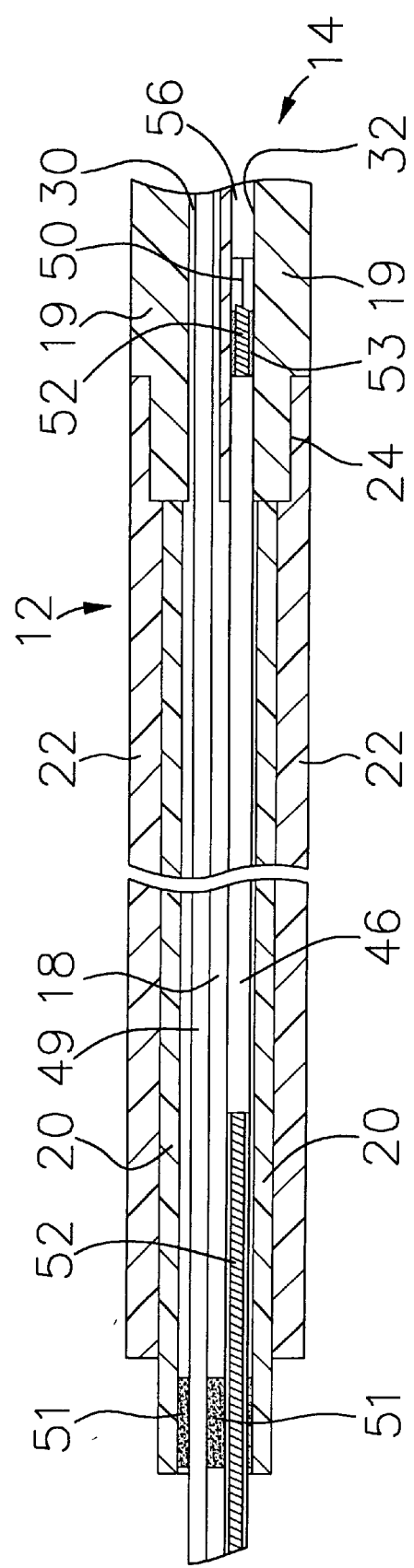
FIG. 2 is a side cross-sectional view of a catheter body according to the invention, including the junction between the catheter body and tip section.
Figure 3:
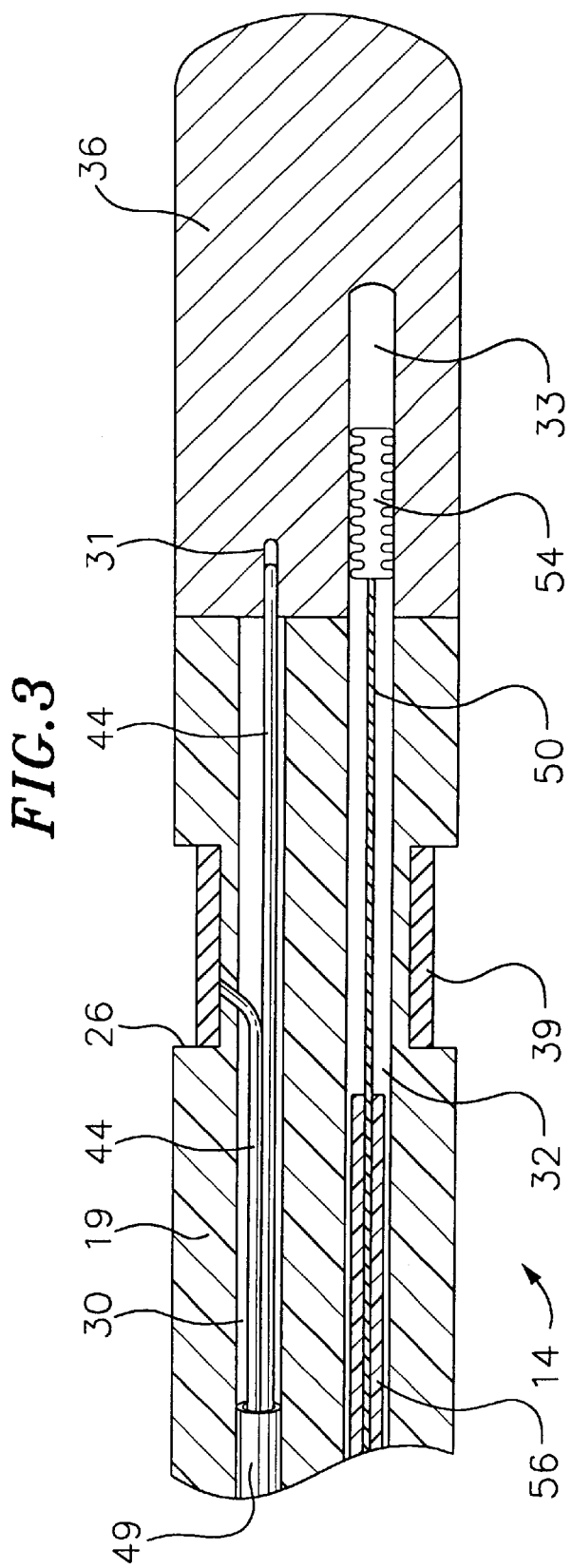
FIG. 3 is a side cross-sectional view of a catheter tip section showing a tip electrode and a recessed ring electrode.

In a particularly preferred embodiment of the invention, there is provided a steerable catheter having two electrodes for making bipolar measurements. As shown in FIGS. 1 to 3, catheter 10 comprises an elongated catheter body 12 having proximal and distal ends, a tip section 14 at the distal end of the catheter body 12, and a control handle 16 at the proximal end of the catheter body 12.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner. The outer diameter of the catheter body 12 is not critical, but is preferably no more than about 8 french (1 mm=3 french), more preferably about 7 french, still more preferably about 5 french. Likewise the thickness of the outer wall 22 is not critical, but is thin enough so that the central lumen 18 can accommodate an infusion tube, a puller wire, lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness. A particularly preferred catheter has an outer wall 22 with an outer diameter of from about 0.090 inch to about 0.098 inch and an inner diameter of from about 0.061 inch to about 0.065 inch and a polyimide stiffening tube 20 having an outer diameter of from about 0.060 inch to about 0.064 inch and an inner diameter of from about 0.051 inch to about 0.056 inch. If desired, the stiffening tube 20 can be eliminated. As would be recognized by one skilled in the art, the catheter body construction can be modified as desired.

As shown in FIG. 3, the tip section 14 comprises a short section of tubing 19 having two lumens 30 and 32. The tubing 19 is made of a suitable non-toxic material that is preferably more flexible than the catheter body 12. A presently preferred material for the tubing 19 is braided polyurethane, i.e., polyurethane with an embedded mesh of braided high-strength steel, stainless steel or the like. The outer diameter of the tip section 14, like that of the catheter body 12, is preferably no greater than about 8 french, more preferably 7 french, still more preferably about 5 french. The size of the lumens is not critical and can vary depending on the specific application.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by adhesive (e.g., polyurethane glue) or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint (not shown) with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint (not shown) is formed between the proximal ends of the stiffening tube 20 and outer wall 22 using a slower drying but stronger glue, e.g., polyurethane.

At the distal end of the tip section 14 is a tip electrode 36. Preferably the tip electrode 36 has a diameter about the same as the outer diameter of the tubing 19. The tip electrode 36 can be made from any suitable material, such as platinum, gold, iridium or stainless steel, and is preferably machined from platinum-iridium bar (90% platinum/10% iridium).

A preferred tip electrode has a length ranging from about 2.5 mm to about 8 mm, preferably about 3.5 mm. Preferably the tip electrode 36 is attached to the tubing 19 by polyurethane glue or the like. The wires that extend into the tip electrode 36, described in more detail below, help to keep the tip electrode in place on the tubing 19 of the tip section 14.

In the embodiment shown in FIG. 3, there is a ring electrode 39 mounted within a circumferential recess 26 in the tubing 19 of the tip section 14. The recess 26 is located near the distal end of the tip section 14 and in close proximity to the tip electrode 36. As used herein, "in close proximity" means a distance suitable for conducting bipolar mapping. Preferably the recess 26 is spaced apart from the tip electrode 36 a distance no greater than about 4 mm, more preferably from about 0.1 mm to about 2 mm, still more preferably from about 0.5 mm to about 1.0 mm. The width and depth of the recess 26 are designed such that, when the tip section 14 is positioned on its side against the adjacent heart tissue, the tissue des not come into contact with the ring electrode 39. Preferably, the width of the recess 26 ranges from about 0.5 mm to about 4 mm, more preferably from about 1 mm to about 3 mm, with the depth of the recess 26 preferably ranging from about 0.25 mm to about 1.5 mm, more preferably from about 0.5 mm to about 1 mm.

In a preferred embodiment, the ring electrode 39 comprises a resilient ribbon-shaped conductive material that is wrapped within the recess 26 and fixed in place by glue or the like. The ring electrode 39 can be made of any suitable conductive material, such as those discussed above for the tip electrode. The width of and thickness of the ring electrode 39 are suitable for fitting within the recess 26 so that the outer surface of the ring electrode 39 is recessed within the recess 26. In other words, the ring electrode 39 has an outer diameter less than the outer diameter of the tubing 19 of the tip section 14. Preferably, the outer diameter of the ring electrode 39 is at least about 10%, more preferably from about 20% to about 50%, less than the outer diameter of the portion of the tip section 14 on which it is mounted. The ring electrode 39 has a width preferably ranging from about 0.5 mm to about 4 mm, more preferably from about 1 mm to about 3 mm. In an alternative embodiment, the ring electrode 39 is in the form of a snap ring, where the width and thickness of the ring 39 are suitable for fitting within the recess 26, as described above.

The tip electrode 36 and ring electrode 39 are each connected to a separate lead wire 44. The lead wires 44 extend through the first lumen 30 of tip section 14, the central lumen 18 of the catheter body 12, and the control handle 16, and terminate at their proximal end in an input jack (not shown) that may be plugged into an appropriate signal processing unit (not shown). The portion of the lead wires 44 extending through the central lumen 18 of the catheter body 12, control handle 16 and proximal end of the tip section 14 may be enclosed within a protective sheath 49, which can be made of any suitable material, preferably polyimide. The protective sheath 49 is preferably anchored at its distal end to the proximal end of the tip section 14 by gluing it in the first lumen 30 with polyurethane glue or the like.

The lead wires 44 are attached to the tip electrode 36 and ring electrode 39 by any conventional technique. Connection of a lead wire 44 to the tip electrode 36 is accomplished, for example, by soldering the lead wire 44 into a first blind hole 31 of the tip electrode, as shown in FIG. 3.

Connection of a lead wire 44 to a ring electrode 39 is preferably accomplished by first making a small hole through the tubing 19. Such a hole can be created, for example, by inserting a needle through the tubing 19 and heating the needle sufficiently to form a permanent hole. A lead wire 44 is then drawn through the hole by using a microhook or the like. The ends of the lead wire 44 are then stripped of any coating and soldered or welded to the underside of the ring electrode 39, which is then slid into position over the hole and fixed in place with polyurethane glue or the like.

A puller wire 50 extends through the catheter body 12, is anchored at its proximal end to the control handle 16, and is anchored at its distal end to the tip section 14. The puller wire 50 is made of any suitable metal, such as stainless steel or Nitinol, and is preferably coated with Teflon® or the like. The coating imparts lubricity to the puller wire 50. The puller wire 50 preferably has a diameter ranging from about 0.006 to about 0.010 inches.

A compression coil 52 is situated within the catheter body 12 in surrounding relation to the puller wire 50. The compression coil 52 extends from the proximal end of the catheter body 12 to the proximal end of the tip section 14. The compression coil 52 is made of any suitable metal, preferably stainless steel. The compression coil 52 is tightly wound on itself to provide flexibility, i.e., bending, but to resist compression. The inner diameter of the compression coil 52 is preferably slightly larger than the diameter of the puller wire 50. The Teflon® coating on the puller wire 50 allows it to slide freely within the compression coil 52. If desired, particularly if the lead wires 44 are not enclosed by a protective sheath 49, the outer surface of the compression coil 52 can be covered by a flexible, non-conductive sheath 46, e.g., made of polyimide tubing, to prevent contact between the compression coil 52 and any other wires within the catheter body 12.

The compression coil 52 is anchored at its proximal end to the proximal end of the stiffening tube 20 in the catheter body 12 by glue joint 51 and at its distal end to the tip section 14 by glue joint 53. Both glue joints 51 and 53 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 52 and wicks around the outer circumference to form a glue joint about the entire circumference of the compression coil 52.

The puller wire 50 extends into the second lumen 32 of the tip section 14. The puller wire 50 is anchored at its distal end to the tip electrode 36 within a second blind hole 33 by weld or the like. A preferred method for anchoring the puller wire 50 within the tip electrode 36 is by crimping metal tubing 54 to the distal end of the puller wire 50 and soldering the metal tubing 54 inside the second blind hole 33. Anchoring the puller wire 50 within the tip electrode 36 provides additional support for the tip electrode on the flexible plastic tubing 19, reducing the likelihood that the tip electrode will separate from the tubing. Alternatively, the puller wire 50 can be attached to the side of the tip section 14. Such a design is described in U.S. patent application Ser. No. 08/924,611 (filed Sep. 5, 1997), the disclosure of which is incorporated herein by reference. Within the second lumen 32 of the tip section 14, the puller wire 50 extends through a plastic, preferably Teflon®, sheath 56, which prevents the puller wire 50 from cutting into the wall of the tubing 19 when the tip section is deflected.

Longitudinal movement of the puller wire 50 relative to the catheter body 12, which results in deflection of the tip section 14, is accomplished by suitable manipulation of the control handle 16. A suitable control handle design for use with the present invention is described in allowed U.S. patent application Ser. No. 08/982,113, filed Dec. 1, 1997, the disclosure of which is incorporated herein by reference.

In operation, the present invention is ideal for mapping the heart and ablating accessory signal pathways causing arrhythmias. To perform this function, the distal end of the catheter 10 is inserted into a vein or artery and advanced into the heart. To assist in positioning the tip section 14 of the catheter 10 at a desired position within the heart, the puller wire 50 and control handle 16 are used to deflect the tip section 14. Once the tip section 14 has been positioned at or near the desired location of the heart tissue, the electrical activity of the heart may be identified, evaluated or mapped, and electrophysiological sources of arrhythmia may be identified and/or treated.

Electrical activity within the heart is detected using the tip electrode 36 and ring electrodes 39 of the catheter 10. The catheter 10 of the present invention is designed such that the tip electrode 36 is in direct contact with the heart tissue. Thus, the tip electrode 36 senses both the local activation energy (near-field signals) at the point of contact with the heart tissue and far field activation energy (far-field signals) received by the electrode through the blood.

As described above, the ring electrode 39 is recessed relative to the tip section 14 to be protected from direct contact with the heart tissue, but permitting contact with surrounding blood. The close proximity of the ring electrode 39 to the tip electrode 36 enables the ring electrode 36 to receive approximately the same far-field signals as the tip electrode 36. However, the ring electrode 39 does not pick up the local activation potential (near-field signals). The signals received by the tip electrode 36 and the ring electrode 39 are sent to a suitable signal processing unit.

Within the signal processing unit, the signal detected by the ring electrode 39, which is only far-field signals, is subtracted from the signal detected by the tip electrode 36, which includes both near-field and far-field signals. Thus, the near-field signals can be more accurately determined. This improved method of detecting electrical activity allows the physician or operator to determine the location of the arrhythmiogenic focus more accurately for ablating and other purposes.

Figure 4:
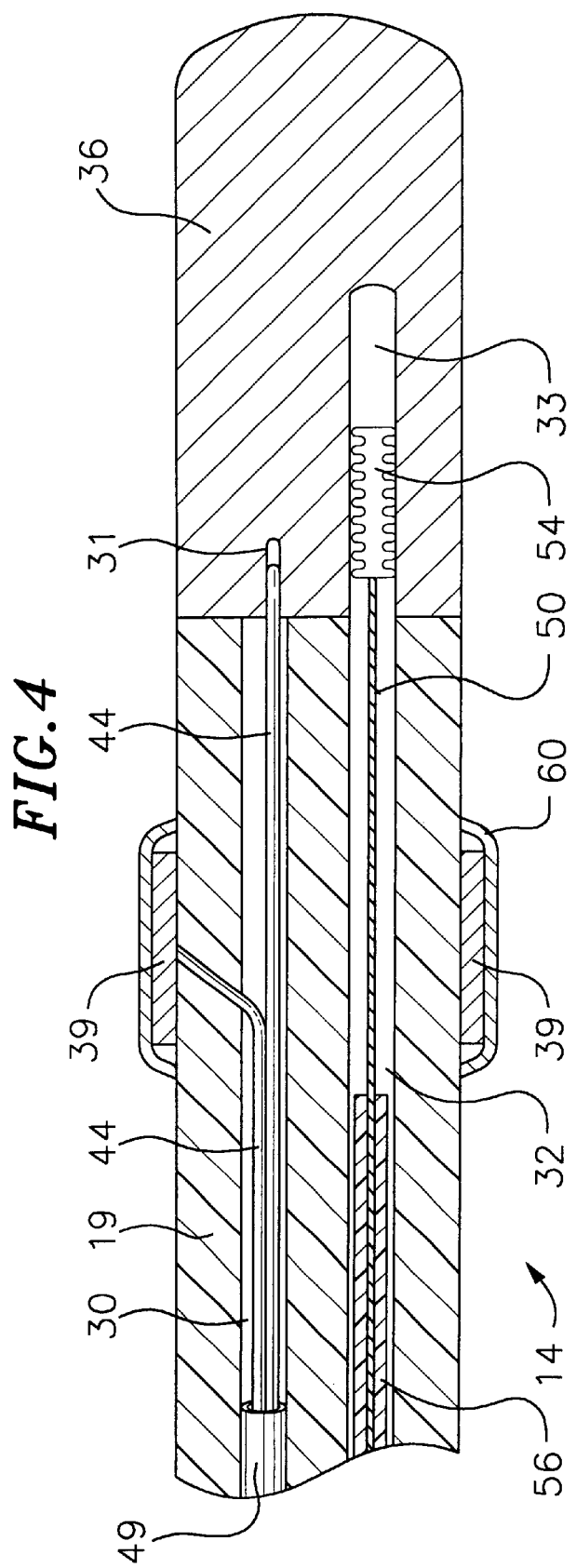
FIG. 4 is a side cross-sectional view of an alternative tip section according to the invention having a ring electrode covered by a blood-permeable material.

Alternate bipolar electrode designs can also be provided having one electrode in contact with blood but not the heart tissue. For example, as shown in FIG. 4, the ring electrode 39 is covered by a membrane 60 that is permeable to the blood, but that prevents direct physical contact between the ring electrode and the heart tissue. In this embodiment the ring electrode 39 is mounted on the tubing 19 proximal to and in close proximity to the tip electrode 39. The ring electrode 39 is slid over the tubing 19 and fixed in place by glue or the like. The membrane 60 is wrapped around the ring electrode 39 and glued in place onto the tip section 14 by polyurethane or the like. The membrane 60 is preferably in the form of a perforated film or a woven or nonwoven fabric. The membrane 60 preferably comprises a biocompatible polymer. Examples of suitable biocompatible polymers for use in connection with the invention include polyolefins such as polypropylene, polyurethane, polyetheramide, polyetherimide, polyimide, fluoropolymers such as polytetrafluoroethylene, silicones and the like, and combinations thereof. The blood-permeable membrane 60 thus allows the blood to permeate the membrane 60 and contact the ring electrode 39, while protecting the ring electrode 39 from direct contact with the heart tissue.

Figure 5A:
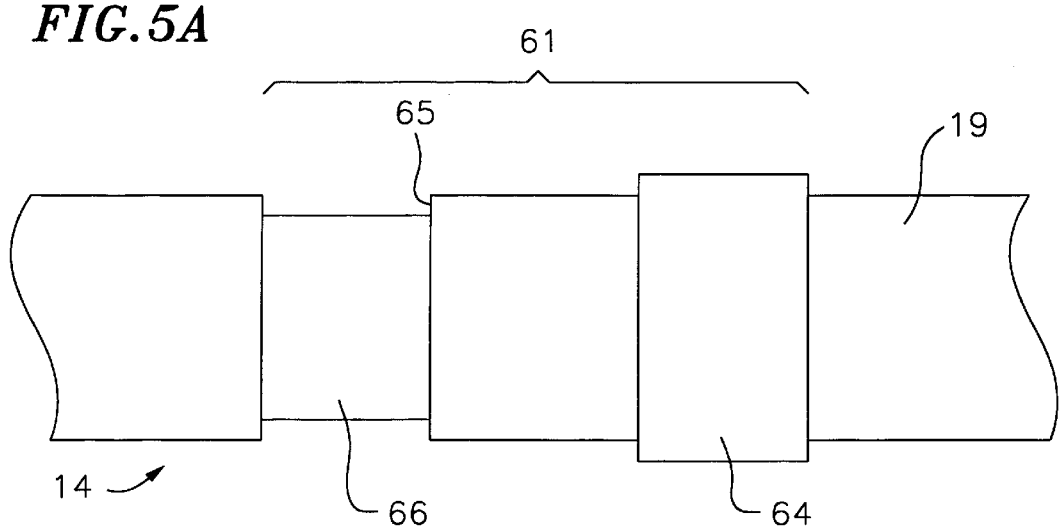
FIG. 5A is a side cross-sectional view of another alternative tip section according to the invention having a first ring electrode and a second ring electrode that is recessed.
Figure 5B:
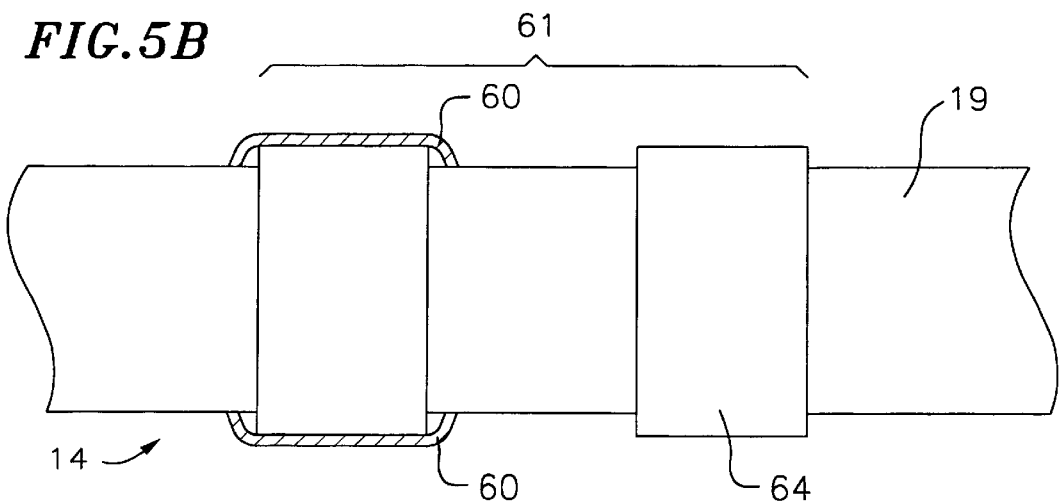
FIG. 5B is a side cross-sectional view of another alternative tip section according to the invention having a first ring electrode and a second ring electrode that is covered by a blood-permeable membrane.

In alternative embodiments, as shown in FIGS. 5A and 5B, ring electrode pairs may be provided instead of the tip electrode/ring electrode combinations described above. In these embodiments, the ring electrode pair 61 includes first and second ring electrodes 64 and 66 mounted in close proximity to each other. In one alternative embodiment, the first ring electrode 64 is mounted on the outer surface of the tubing 19 to make direct contact with adjacent heart tissue. The second ring electrode 66 is displaced within a recess 65 proximal to the first electrode 64 such that the second electrode 66 is recessed from the outer surface of the tubing 19 to prevent direct contact with adjacent heart tissue, in a manner as described above.

In another alternative embodiment, the first ring electrode 64 is mounted on the outer surface of the tubing 19, to make direct contact with adjacent heart tissue. The second ring electrode 66 is mounted on the tubing 19 proximal to the first electrode 64. A blood-permeable membrane 60 is wrapped around the second electrode 66, in a manner as described above, to protect the second electrode 66 from direct contact with adjacent heart tissue.

As would be recognized by one skilled in the art, the relative locations of the ring electrodes can vary. For example, in the embodiment of FIG. 5A, the second electrode 66, which is recessed, can be distal to the first electrode 64. Also, additional ring electrodes can be provided for any of the above-described embodiments.

Figure 6:
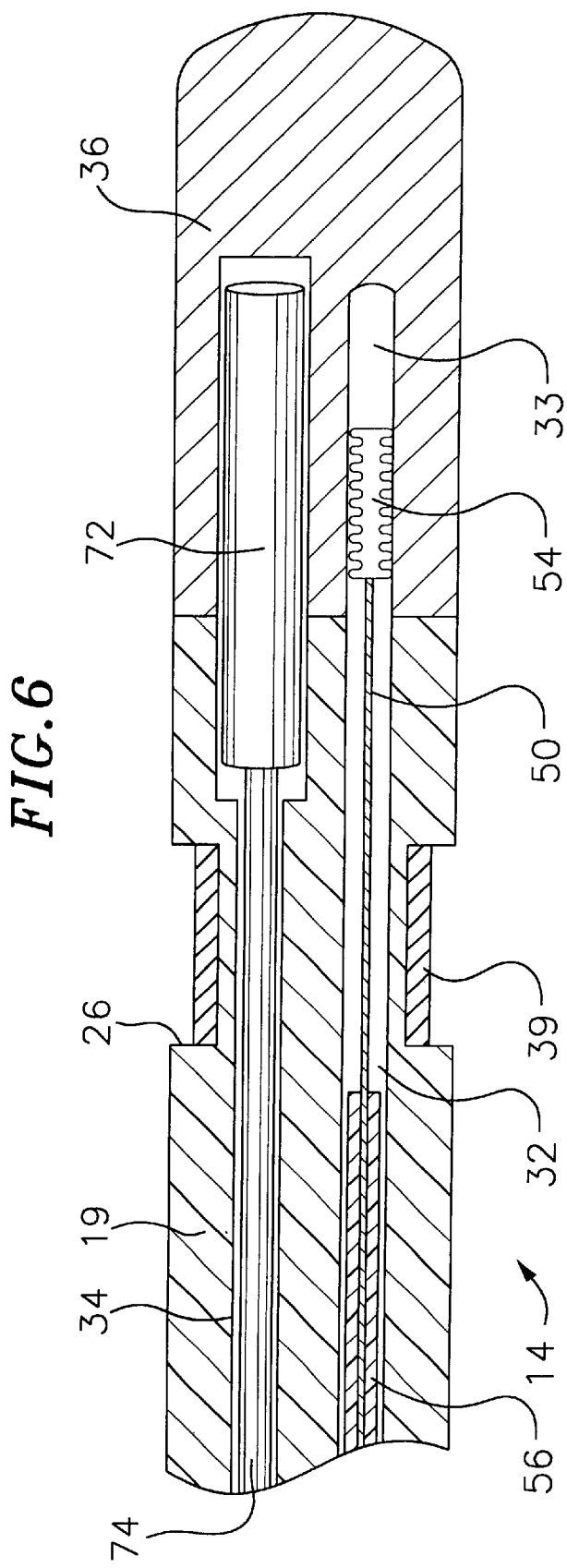
FIG. 6 is a side cross-sectional view of another alternative tip section according to the invention, the tip section including an electromagnetic location sensor.

In an alternative embodiment, the catheter further includes a location sensor, preferably an electromagnetic location sensor. As shown in FIGS. 6 and 7, the tip section 14 includes a third lumen 34. The electromagnetic sensor 72 is mounted in part in the distal end of the tubing 19 and in part in a blind hole in the tip electrode 36. Suitable electromagnetic sensors for use in connection with the present invention are described in U.S. patent application Ser. No. 09/160,063 (entitled "Miniaturized Position Sensor") and U.S. Pat. Nos. 5,558,091, 5,443,489, 5,480,422, 5,546,951, 5,568,809, and 5,391,199, the disclosures of which are incorporated herein by reference. The electromagnetic sensor 72 is connected to a electromagnetic sensor cable 74, which extends through the third lumen 34 of the tip section 14, through the central lumen 18 of the catheter body 12, and into the control handle 16. The electromagnetic sensor cable 74 then extends out the proximal end of the control handle 16 within an umbilical cord (not shown) to a sensor control module (not shown) that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The electromagnetic sensor cable 74 comprises multiple wires encased within a plastic covered sheath. In the sensor control module, the wires of the electromagnetic sensor cable are connected to the circuit board. The circuit board amplifies the signal received from the electromagnetic sensor and transmits it to a computer in a form understandable by the computer by means of the sensor connector at the proximal end of the sensor control module. Also, because the catheter is designed for single use only, the circuit board preferably contains an EPROM chip which shuts down the circuit board approximately 24 hours after the catheter has been used. This prevents the catheter, or at least the electromagnetic sensor, from being used twice. If desired, the sensor 72 can be contained within a rigid plastic housing, e.g., made of polyetheretherketone (PEEK), that is mounted between the tip electrode 36 and the flexible tubing 19. Such a design is described in U.S. Pat. No. 5,938,603, the disclosure of which is incorporated herein by reference.

To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the catheter containing a the electromagnetic location sensor is advanced into the patient's heart. Each sensor preferably comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of that catheter that is caused by contraction of the heart muscle. A preferred mapping system includes a catheter comprising multiple electrodes and an electromagnetic sensor, such as the NOGA-STAR catheter marketed by Biosense Webster, Inc., and means for monitoring and displaying the signals received from the electrodes and electromagnetic sensor, such as the Biosense-NOGA system, also marketed by Biosense Webster, Inc.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved. By combining the electromagnetic sensor and electrodes, a physician can simultaneously map the contours or shape of the heart chamber and the electrical activity of the heart.

If desired, the catheter can be multidirectional, i.e., having two or more puller wires to enhance the ability to manipulate the tip section in more than one direction or to form two or more different curves. A description of such a design is described in U.S. patent application Ser. Nos. 08/924,611 (filed Sep. 5, 1997), 09/130,359 (filed Aug. 7, 1998), 09/143,426 (filed Aug. 28, 1998), 09/205,631 (filed Dec. 3, 1998), and 09/274,050 (filed Mar. 22, 1999), the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for measuring near-field electrical activity at a location in a heart comprising:
   introducing into the heart a catheter comprising:
      an elongated tubular body having a distal region and a circumferential recess along the length of the distal region,
      a first electrode mounted on the distal region in close proximity to the circumferential recess, and
      a second electrode mounted within the circumferential recess, the second electrode being configured such the second electrode is not in direct contact with heart tissue but is in contact with blood when the distal region is positioned against heart tissue at a side of the distal region;
   positioning the distal region at the location in the heart so that the first electrode is in direct contact with heart tissue;
   obtaining a first signal with the first electrode;
   obtaining a second signal with the second electrode;
   comparing the first signal and the second signal to obtain the near-field electrical activity at the location in the heart.

2. A method as claimed in claim 1, wherein the first electrode is a tip electrode.

3. A method as claimed in claim 1, wherein the first electrode is a ring electrode.

4. A method as claimed in claim 1, wherein the second electrode is mounted a distance from the first electrode ranging from about 0.1 mm to about 2.0 mm.

5. A method as claimed in claim 1, wherein the second electrode is mounted a distance from the first electrode ranging from about 0.5 mm to about 1.0 mm.

6. A method as claimed in claim 1, wherein an outer diameter of the second electrode is from about 20% to about 50% of an outer diameter of a portion of the distal region.

7. A method as claimed in claim 1, wherein the catheter further comprises a location sensor.

8. A method as claimed in claim 7, further comprising acquiring near-field electrical activity information with the first and second electrodes and location information with the location sensor at a plurality of locations within the heart.

9. A method as claimed in claim 8, further comprising generating a map of the electrical activity of the heart using the acquired near-field electrical activity information and location information.

10. A method as claimed in claim 7, wherein the location sensor is an electromagnetic location sensor.

11. A method for measuring near-field electrical activity at a location in a heart comprising:
   introducing into the heart a catheter comprising:
      an elongated body having an outer diameter and a distal region,
      a first electrode mounted on the distal region, and
      a second electrode mounted on the distal region in close proximity to and electrically isolated from the first electrode, the second electrode having an outer diameter less than the outer diameter of the portion of the distal region on which it is mounted;
   positioning the distal region at the location in the heart so that the first electrode is in direct contact with heart tissue and the second electrode is not in direct contact with heart tissue but is in contact with blood;
   obtaining a first signal with the first electrode;
   obtaining a second signal with the second electrode;
   comparing the first signal and the second signal to obtain the near-field electrical activity at the location in the heart.

12. A method as claimed in claim 11, wherein the first electrode is a tip electrode.

13. A method as claimed in claim 11, wherein the first electrode is a ring electrode.

14. A method as claimed in claim 11, wherein the second electrode is mounted a distance from the first electrode ranging from about 0.1 mm to about 2.0 mm.

15. A method as claimed in claim 11, wherein the second electrode is mounted a distance from the first electrode ranging from about 0.5 mm to about 1.0 mm.

16. A method as claimed in claim 11, wherein the outer diameter of the second electrode is from about 20% to about 50% of the outer diameter of the portion of the distal region on which it is mounted.

17. A method as claimed in claim 11, wherein the catheter further comprises a location sensor.

18. A method as claimed in claim 17, further comprising acquiring near-field electrical activity information with the first and second electrodes and location information with the location sensor at a plurality of locations within the heart.

19. A method as claimed in claim 18, further comprising generating a map of the electrical activity of the heart using the acquired near-field electrical activity information and location information.

20. A method as claimed in claim 17, wherein the location sensor is an electromagnetic location sensor.

* * * * *